United States Patent [19]

Samyn

[11] Patent Number: 4,566,121

[45] Date of Patent: Jan. 21, 1986

[54] PROCESS AND APPARATUS FOR IDENTIFYING ARTICLES OF SHEET MATERIAL BY MEANS OF MICROWAVES

[76] Inventor: Johan Samyn, Oostnieuwkerksesteenweg 199, 8800 Roeselare, Belgium

[21] Appl. No.: 481,242

[22] Filed: Apr. 8, 1983

[30] Foreign Application Priority Data

Jul. 29, 1982 [LU] Luxembourg .......................... 84308

[51] Int. Cl.[4] ......................... G06K 9/00; G01R 27/04
[52] U.S. Cl. .................................. 382/7; 324/58.5 R; 340/600; 382/58
[58] Field of Search ............... 209/534, 536, 576, 589; 250/271, 555–559, 562–563, 566, 571–572; 356/71–73; 343/5 PD; 427/7; 428/916; 340/673–675, 600; 235/439–440, 487, 491; 324/58.5 R, 58.5 A, 58.5 B; 162/146; 382/7, 58

[56] References Cited

U.S. PATENT DOCUMENTS

| 3,506,829 | 4/1970 | Hannan | 250/271 |
| 3,851,971 | 12/1974 | Koch | 356/398 |
| 4,183,989 | 1/1980 | Tooth | 428/916 |
| 4,265,703 | 5/1981 | Terliska | 162/146 |
| 4,352,988 | 10/1982 | Ishida | 250/559 |
| 4,368,421 | 1/1983 | Glander et al. | 324/58.5 A |
| 4,408,156 | 10/1983 | Veys | 324/58.5 R |

FOREIGN PATENT DOCUMENTS

| 2037755 | 2/1972 | Fed. Rep. of Germany | 356/71 |
| 2062854 | 5/1981 | United Kingdom | 209/534 |

Primary Examiner—Leo H. Boudreau
Attorney, Agent, or Firm—Shlesinger Arkwright Garvey & Fado

[57] ABSTRACT

An apparatus for the identification by microwaves of a sheet article composed of an electrically non conductive material, the article being marked for identification by the incorporation therein of electrically conductive fibers. The apparatus comprises at least two microwave emitter devices one adjacent the other with detectors for the waves reflected by the article when advanced before said devices. The apparatus comprises also detectors for the waves transmitted through the article and placed in front of said emitter devices. Regulating methods of the apparatus are also described for raising the sensitivity of the identification signals through setting of the distances between the emitter devices, detectors for transmitted waves and support for the interposed article.

15 Claims, 4 Drawing Figures

PROCESS AND APPARATUS FOR IDENTIFYING ARTICLES OF SHEET MATERIAL BY MEANS OF MICROWAVES

This invention relates to a method and apparatus of identifying sheet or plate articles composed of electrically non-conducting materials by means of microwaves, the article being marked for identification by the incorporation of electrically conductive fibrous materials.

BACKGROUND OF THE INVENTION

One known method of marking sheet articles is to use, for example, paper sheets comprising small amounts of very thin metallic fibres distributed in the sheets and capable of absorbing and reflecting certain proportions of the energy of microwave radiation impinging on them. Therefore, it has been considered to apply this property to, among other things, certain types of security paper, such as banknotes, passports and bonds for their identification or verification of their authenticity by traversing them on a support through the path of a microwave emitter device and by detecting and measuring the proportion of the energy reflected and absorbed by the electrically conductive fibres embedded in the sheets. The amount of conductive fibres must remain small so as not to significantly change the aspect and properties of the sheets or plates. It has been described in the French Patent Application No. 80,09095 of Applicant that fibres with smooth surfaces possessing a conductivity inferior to 10% of that of the standard of copper, with a diameter inferior to 50 $\mu m$ and a length of less than 10 mm, produce an excellent microwave identification signal at quantities of e.g. 0.5% by weight in the article. These fibres produce a specific response which can hardly be imitated by other materials so that counterfeiting the marking is prevented. Moreover, it is generally desirable that the microwave detection device be very sensitive and capable of rapid response, and permit reproducible identifications of the same article.

BRIEF DESCRIPTION OF THE INVENTION

It is an object of the invention to provide a simple and compact apparatus for high-speed identification of the above described articles by detecting the waves reflected by the article when the microwaves released by at least one first and at least one second microwave device placed in front of the article, impinge on it and by additionally detecting the energy of the waves transmitted through the article. According to an important characteristic of the invention each microwave device comprises an emitter, a circulator or a directional coupler in which a fraction of the reflected waves are deviated towards a detector of said reflected waves. Apart from the microwave devices, the apparatus also comprises wave detectors of the transmitted waves placed in front of the microwave devices. A support for the article is placed between said microwave devices and said detectors of the transmitted waves. In order to raise (or at least optimize) the sensitivity of the identification signals it is necessary, according to the invention, to adjust the respective distances between the microwave devices and the detectors in front of them, and between the microwave devices and the support, e.g. to position each said detector and the support with respect to said microwave device. Therefore the apparatus also comprises means for adjusting the respective distances, e.g. the positioning of its component elements. Another specific object of the invention is to provide regulating methods for the apparatus, especially for positioning the elements. The use of high-frequency microwaves (e.g. as from 10 GHz) improves the sensitivity of the detection.

According to a preferred embodiment, the apparatus may comprise various consecutive first and second microwave devices with different polarization of the waves emitted between said first and said second devices and through whose path the article carried by its support is passed.

BRIEF DESCRIPTION OF THE DRAWINGS

The invention will now be described with reference to the adjoined drawings which refer to appropriate embodiments. At the same time, the working of the apparatus, specific characteristics and advantages of the invention will be explained in greater detail.

DETAILED DESCRIPTION

Figure 1:
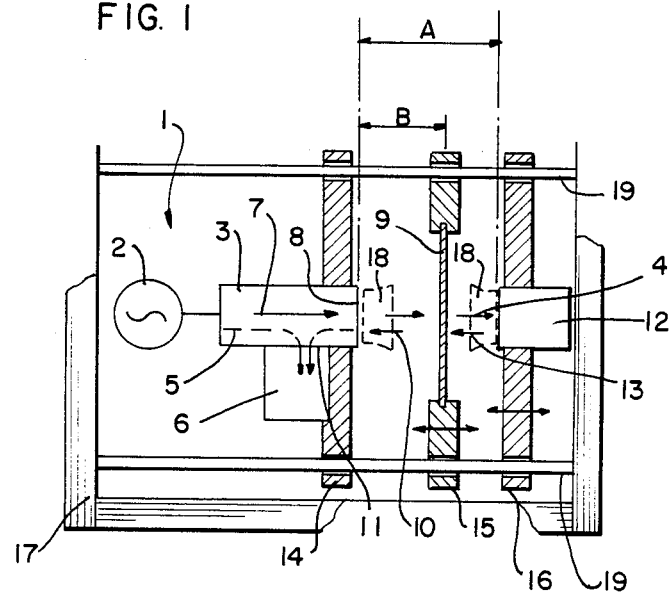
FIG. 1 is a schematic view of the positioning of the basic elements of the apparatus.

The apparatus according to FIG. 1 essentially comprises a microwave device 1. This device is composed of a microwave emitter 2 linked to a circulator 3 (to which an antenna 8 may be connected).

The emitter 2 may be a Gunn oscillator using a Gunn diode in a resonant cavity for producing microwaves with a frequency of more than 1 GHz, e.g. 25 GHz (wave length 12 mm). Oscillators of this type are commercially available. The output of the resonant cavity is connected with e.g. a ferrite circulator 3, commonly used in microwave transceivers for microwave reflection control systems. Such a circulator 3 is not ideal since a fraction 5 of the entering waves is deviated towards the detector 6 linked to the circulator. A plane polarized microwave beam 7 is emitted at port 8 of the circulator and launched against the sheet or plate article 9 placed with its surface perpendicularly to the direction of the beam 7. A portion of the waves impinging on the article is reflected by it on account of the presence of electrically conducting fibrous material in the article and enters port 8 in the opposite direction. These reflected waves 10 are subsequently transmitted by port 11 of the circulator towards the detector 6 of the reflected waves. The detector 6 may be a known Schottky diode. Another fraction 4 of the waves impinging on the article is transmitted and captured (or detected) by the detector 12 which can also be provided with an antenna 18. The detector 12 of the received waves may also be a Schottky diode. Finally, a third fraction of the energy impinging on the article is absorbed by the electrically-conductive fibres present in the article. Nevertheless, since the detector 12 comprises metallic parts, a fraction of the transmitted waves does not enter the detector 12, but it is reflected by these metallic parts (waves 13) against the article 9. A portion of the reflected waves 13 is then transmitted by the article and this transmitted portion is added to the portion of directly reflected waves 10 which enter port 8 in order to be captured by the detector 6. (Another fraction of the reflected waves 13 is absorbed by the electrically conductive fibres.)

The superposition of these direct, reflected, transmitted and repeated reflection waves with different phases leads to the creation of standing waves as well at the entry 11 of the detector 6 as at that of the detector 12.

The use of a non-ideal circulator 3 as described above also permits the creation of specific standing waves in the detector cavity. These waves are the results of a superposition of deviated waves 5 and reflected waves 10 and the creation of these standing waves makes it possible to produce a unique detection signal whose sensitivity can be regulated according to need. The regulating methods for the apparatus and for raising the sensitivity of the identification signal through the reflection of waves from the article are based on the phenomenon of these standing waves.

The apparatus is regulated by adjusting the respective distances A and B between the microwave device 1 and the detector 12 and between the device and the support 15. In fact, changing these distances will cause a phase shift of the reflected and transmitted waves as compared with the phase of the emitted waves. The superposition of the shafted waves will create another standing wave pattern as a function of the change of these distances. The elements 1, 9 and 12 are supported in their respective supporting frames 14, 15 and 16, and changing the respective distances is done, for example, by sliding these frames on positioning bars 19 mounted in the frame 17 of the apparatus.

Figure 2:
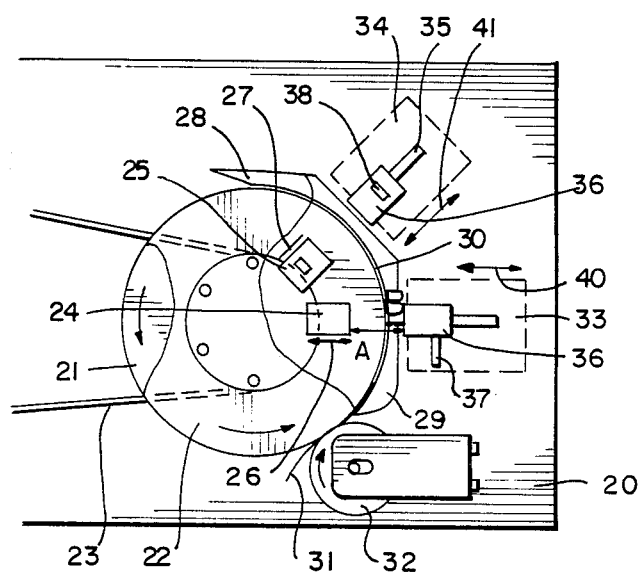
FIG. 2 is a view of a continuous detection system comprising two microwave devices with different polarization.

The apparatus shown in FIG. 2 concerns an example of an apparatus comprising traversing means for moving the article on its support. In general, this is the type of apparatus used for automatic continuous sorting machines for documents such as banknotes. In a frame 20 two parallel discs 21, 22 are mounted at a given distance apart on a shaft. This intermediate space comprises the pulley driving the discs and put in motion by means of the belt 23, and the wave detectors 24, 25 of transmitted waves. The wave detectors 24, 25 are fixed by one of their ends in non-illustrated positioning means. The positioning possibility is suggested by the arrows 26, resp. 27.

Opposite a portion of the respective circumferences of the discs 21, and 22, there are fixed elements 28, 29 with surfaces curved concentrically to the disc circumferences. The discs and these elements form a passage 30 for the documents 31 to be checked. The documents 31, comprising electrically conductive fibres, are introduced in the passage between the discs 21, 22 and a roller 32, and subsequently pushed forward in the path in front of the adjacent first microwave devices 33, respectively second devices 34. Each such device comprises an oscillator 35, a circulator 36 and a detector 37, respectively 38 for the reflected waves. According to an embodiment, the plane of polarization of the waves emitted by one of the first microwave devices is taken different from the plane of polarization of the waves emitted by a second one. In this case, the polarization plane of the waves emitted by one of the devices 33, 34 is preferably essentially parallel to the traversing direction of the documents 31, while the polarization plane of the other device is essentially perpendicular to this direction.

Another possibility is to select the direction of the plane of the waves received by at least one of the detectors of transmitted waves different from that of the plane of polarization of the waves emitted by the microwave device placed in front of this detector. If the directions of the plane of the waves received by said detector is selected different from that of the plane of polarization of the waves from the microwave device in front of the detector, it is preferable that these two planes cross at a 90-degree angle in order to create a maximum signal contrast in the respective detectors between the reflected waves and the waves transmitted to the detector. Either of the planes may then be oriented essentially parallel to the traversing direction of the article.

As an alternative the apparatus can be conceived as having the plane of the waves received by at least one of the first detectors of transmitted waves different from the plane of the waves received by a second said detector. The plane of polarization of the waves received by at least one of the first detectors can then be fixed preferably parallel to the traversing direction of the article 31, while the plane of polarization of a second detector is selected essentially perpendicular to this direction or vice versa. Moreover, to this combination a situation may be added where the planes of the waves emitted by at least one first and at least one second device (33, resp. 34) are parallel to the planes of the waves received by the first, resp. second detectors 24, resp. 25 placed in front of the respective microwave devices.

In order to regulate the respective desirable orientations of the planes of polarization of the waves emitted by the different microwave devices, as well as of the waves transmitted to the detectors, the apparatus will, in general comprise conventional and non-illustrated means for adjusting the angular position of rotation of the microwave devices and/or detectors about an axis parallel to the direction of propagation of the emitted waves.

The apparatus is regulated as follows: first the distance A is adjusted in absence of the article 9, 31 between each of the microwave devices 1, 33, 34 and the detectors of transmitted waves 12, 24, 25 placed in front of these respective devices, in order to obtain in said detectors a predetermined transmission signal level. It has already been explained above that the emitted waves and the waves reflected by the metallic parts of the detectors (with different phases) are superimposed to form a standing wave. By changing the distance A one can select the level of the transmitted signal registered by the detector. This detector is of the same type as that (6, 37, 38) fixed to the microwave devices. Preferably, the distance A will be fixed so as to obtain a maximum transmission signal level.

Subsequently, this distance A is readjusted in the absence of the article by means of a small displacement of either the detector in front of the device or of the device itself so as to obtain in said detectors 6, 37, 38 a predetermined reflection signal level. Said detectors and the microwave devices are fixed at this intermediate distance. Preferably, said detector (or microwave device) will be moved over this minimum distance so as to obtain a minimum reflection signal level in said detector 6, 37, 38. Afterwards, this reflection signal is considered as reference reflection signal. The readjustment has the supplementary effect that the formerly set maximum level (at distance A) has slightly diminished. The level of the transmissioon signal registered by the detector at this readjusted distance is considered as reference transmission signal.

After having placed the article 9, 31 in its support between the detector 12, 24, 25 and the microwave device 1, 33, 34, the distance B between the microwave devices and support (carrying the article) is regulated—thereby obviously respecting the readjusted distance A between the microwave devices and the detectors—so as to produce in said detectors 6, 37, 38 a reflection signal level substantially different from those obtained in the absence of the article. The support is fixed in this position.

For regulating the distance B, preferably the respective elements will be positioned so as to obtain in the detectors of reflected waves a maximum reflection signal level. As described above the interposition of the article 9, 31 between the microwave devices and the detectors of transmitted waves creates a superposition phenomenon in the form of a complex of direct waves, reflected waves and waves transmitted at different phases. The result of this superposition produces a standing wave which allows to fix the reflection signal level as a function of the distance B.

EXAMPLE 1

A prototype of paper banknote 31 was prepared according to a process described in the French Patent Application No. 78.14617. Throughout the surface of the paper 4% by weight of Bekinox ® stainless steel fibres of Applicant with a diameter equivalent to 12 micron and a length of 5 mm are dispersed. In the course of the continuous manufacture of the paper on an industrial installation, the electrically conductive fibres were slightly oriented in the forward direction of the fresh layer of paper through the machine. This phenomenon seems to be characteristic for industrial paper fabrication and it is almost inimitable by manual or semi-industrial processes. The paper was cut into rectangular notes with the length of the rectangle parallel to the forward direction of the paper during manufacture. The note measured 17.2 cm to 7.5 cm. The note was introduced in the passage 30 around a disc drum 21, 22 of an automatic Crossfield sorting machine with a speed of 10 m/sec between a microwave device 33 and a detector 24. The oscillator 35 was of the type (Microwave Associates) MA 86790, while for the detectors 37 and 34 Shottky MA 86561 diodes were used. The rectangular port 8 of the circulator had a length of 4.1 mm and a width of 2 mm. The polarization plane of the emitted microwaves was perpendicular to the length of the rectangular port. The emitted microwaves had a frequency of 25 GHz (wavelength 12 mm) and were polarized in a plan parallel to the forward direction of the banknote 31. The rectangular port of the reflection and transmission detectors was 10 mm long and 4 mm wide. The plane of polarization of the received (transmitted) waves was also perpendicular to the length of this rectangular port. The plane of polarization of these received waves was taken parallel to the forward direction of the banknote.

The distance A was determined in the absence of the banknote. The position is suggested by the arrows 26 and 40 so as to obtain in the detector 24 a maximum transmission signal level. After readjusting the distance A so as to obtain a minimum reflection signal level in the detector 37 (in the absence of the article), the readjusted distance was 27 mm.

Finally, the banknote 31 was placed in its passage 30 and by respecting the distance A fixed as described above, the distance B was selected so as to obtain in the detector 37 a maximum reflection signal level. The distance B was 17 mm.

Figure 3:
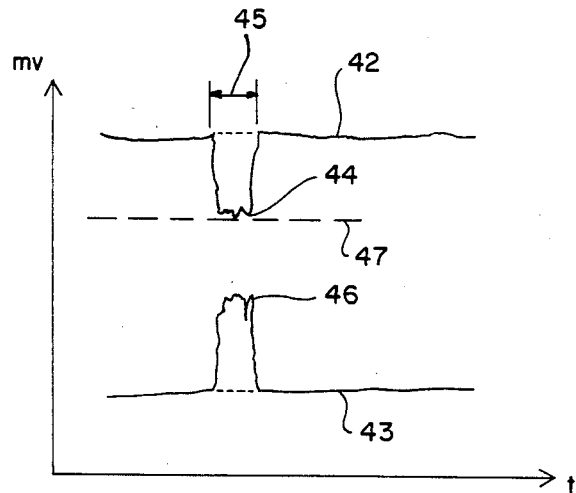
FIG. 3 shows the detected signals reflected and transmitted by a sheet comprising metallic fibres.

FIG. 3 now shows the signals received by an oscilloscope for the prototype of the banknote described above. The abscissa represents the time and the ordinate a measure proportional to the reflected energy. Line 42 corresponds with the nearly maximum transmission signal level (after readjusting distance A) registered by the detector 24. The transmission in the air (reference signal) of the apparatus: 77 mV. Line 43 corresponds with the minimum reflection signal level registered in detector 37 at the readjusted distance: the reflection in the air (reference signal) of the apparatus. The peak 44 corresponds with the nearly zero transmission, level 47 (7 mV) which was registered during the passage of the banknote in front of the detector. The width 45 of this peak corresponds more or less to 17.5 milliseconds for the time of passage of the note in front of the microwave emitter at a speed of 10 m/sec. On the other hand, the peak 46 points to an important reflection level: 90 mV on average.

On account of the composition of the banknote, one might have expected these type of signals since the length, diameter, concentration and orientation of the fibres in the direction of polarization of the waves suggests a strong reflection and nearly negligible transmission.

EXAMPLE 2

Figure 4:
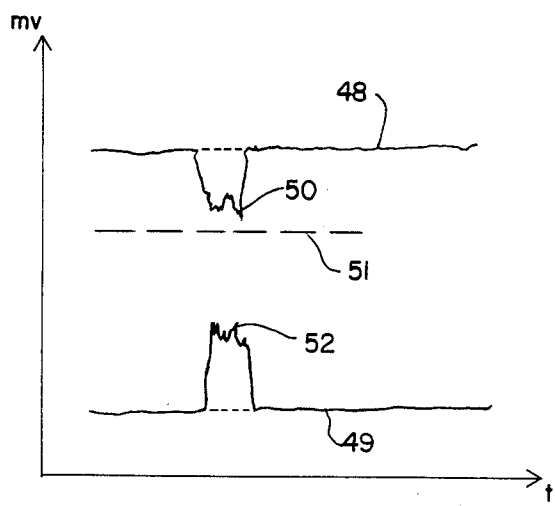
FIG. 4 refers to similar signals from a sheet comprising other metallic fibres.

Another prototype of banknote 31 was prepared in a (non-industrial) laboratory. Throughout the surface of the paper 1% by weight of Bekinox ® fibres with a diameter of 8 micron and a length of 3 mm were dispersed substantially uniformly. The fibres were oriented at random in the paper. The note's dimensions were 19.2 cm to 7.4 cm and were fed into the same Crossfield automatic sorting machine as used in the first example working at the same speed. The elements, the frequency, the polarizations and the distances A and B were also the same. FIG. 4 shows the examination signals of this banknote. The line 48 shows the maximum level of transmission in the air of the apparatus (77 mV) and the line 49 the minimum level of reflection in the air. The peak 50 approximates the line 51 of zero transmission though it points to a transmission level of 22 mV which is much higher than in the example 1. On the contrary, the average reflection level indicated by the peak 52 has dropped to 74 mV. The fibres being smaller, oriented more at random and with a smaller concentration, one might have expected a lower reflection level as compared with that of the first example. On the other hand, the considerable increase of the transmission level suggests that the fibres are not dispersed very uniformly throughout the surface, i.e. there are "gaps" in the banknote in those spots where there are not enough electrically conductive fibres. Indeed, it is very difficult to guarantee a perfect distribution of the metallic fibres in paper formats produced manually in laboratories.

Although the invention has been described with reference to the apparatus shown in the Figures, it must be understood that it is not limited to these embodiments. The frequency of the microwaves may differ from one microwave device to another. A first microwave device, for example, may operate at 25 GHz and the second one, for example, at 10 GHz. A higher frequency implies a more accurate and delicate positioning since the wave length of standing waves is half that of the emitted waves. Instead of traversing the article subsequently in the path of first and second microwave devices, one may conceive, for example, to pass it twice through the path of the same microwave device by changing between both passages either the orientation of the article, or the orientation of the plane of polarization of the microwave device, or that of the wave detector placed in front of this device.

It is also evident that the detection signal may produce a command through the intervention of a relay or other actuator in order to eliminate from a continuous series of examined articles those which do not correspond with the set standards. In the practice of automatic sorting of banknotes, for example, this measure would permit to eliminate counterfeited banknotes automatically.

The sheet of plate articles may either be fibrous structures such as paper, non-woven articles, fabrics, yarns, or non-fibrous structures, for example based on plastic or ceramic materials, or laminated combinations of these structures. During manufacture they may be marked only by the local embedment of electrically conductive fibrous materials.

The use of fibrous materials, other than the Bekinox ® stainless steel fibres of Applicant, is possible. Nevertheless, the electrical conductivity of these Bekinox ® fibres is almost ideal for the identification system according to the invention since it offers absorption and reflection characteristics of the same order of magnitude. Hence, these values may be detected by the same type of detectors. Moreover, the small fiber diameter offers a maximum absorption capacity in the detection circumstances according to the invention, e.g. by selecting a good combination of geometry and (low) concentration of the fibres as a function of the frequency of the microwave devices. The small diameter of the fibers also favours the aspect of the article, e.g. security paper. Further a regular surface of the fibres avoids variations in the detection signal.

By using the fibres with fairly high conductivity and by respecting the fibre dimensions (diameter under 25 micron, length under 10 mm) as well as the order of magnitude of the concentration of these fibres in the article (less than 5% by weight), the articles will offer absorption values that are too weak and reflection values that are too high so that they can no longer be distinguished from plates or metallic layers with the system according to the invention.

On the other hand, by using fibres with a very weak conductivity, (lower than that of said Bekinox ® fibres) it will be necessary to incorporate thicker fibres (in order to reach an unneglible absorption level) which would deteriorate the aspect of the article.

If the surface of the articles is fairly large and the marking, for example, limited to limited places in the surface, it is evident that various combinations of transceivers must be mounted in the apparatus one next to the other in order to permit a proper examination of the entire surface.

All these variants as well as others known to anyone skilled in the art are considered to be part of the invention and covered by the following claims.

I claim:

1. An apparatus for the identification of a sheet or plate article, the article being composed of an electrically non-conductive material and being marked for identification by the incorporation of electrically conductive materials, comprising: a frame; at least one first and at least one second microwave device, for producing waves, said first and second device being mounted on said frame one adjacent the other; at least one first and one second detector of waves transmitted by the article when the article is advanced before said devices, said detectors being placed in front of the respective microwave devices so, when the article is advanced, the article traverses each said detector and respective device in a traversing direction; a support for the article, said support positioned between said devices and said detectors; a circulator means or directional coupler means, associated with each said microwave device, for deviating waves reflected by the article towards a detector of said reflected waves; and, adjusting means for adjusting the respective distance between said microwave devices and said detectors of transmitted waves and said microwave devices and said support.

2. An apparatus according to claim 1, comprising an addition traversing means for moving the article carried by the support.

3. An apparatus according to claim 1 or 2, wherein the plane of polarization of the waves emitted by a first device is different from the plane of polarization of the waves emitted by a second device.

4. Apparatus according to claim 3, whereby the plane of polarization of the waves emitted by a first microwave device is essentially parallel to the traversing direction of the article, while the plane of polarization of a second microwave device is essentially perpendicular to that direction.

5. An apparatus according to the claim 1 or 2, whereby the direction of the plane of waves received by at least one of the (first) detectors for the waves transmitted is different from the direction of the plane of the waves received by a second said detector.

6. An apparatus according to claim 5, whereby the plane of the waves received by at least one of the first detectors is essentially parallel to the traversing direction of the article while the plane of the waves received by a second said detector is essentially perpendicular to this direction.

7. An apparatus according to the claim 5 whereby the plane of the waves emitted by at least one first and at least one second microwave device is parallel to the plane of the waves received by the first and second detectors placed in front of the respective microwave devices.

8. An apparatus according to claim 1 wherein the direction of the plane of the waves received by at least one of the detectors of transmitted waves is different from that of the plane of polarization of the waves emitted by the microwave device placed in front of this detector.

9. An apparatus according to claim 8, whereby the plane of the waves received by at least one of the detectors is perpendicular to the plane of waves emitted by the microwave device placed in front of this detector.

10. An apparatus according to claim 1 whereby it also comprises adjusting means for the angular position of rotation of microwave devices and/or detectors around an axis parallel to the direction of propagation of the emitted waves.

11. An apparatus according to claim 1 wherein it further comprises actuator means which respond to the identification signals produced by the first and second detectors of transmitted and reflected waves and which eliminate the non standardized sheet articles in a continuous series of examined articles.

12. A method for regulating an apparatus for the identification of a sheet or plate article, the article composed of an electrically non-conductive material, the article being marked for the identification by the incorporation of electrically conductive materials, the apparatus including at least one first and at least one second microwave device for producing waves, at least one first and one second detector of transmitted waves, at least one first and one second detector of reflected waves and a support for the article, comprising the steps of:

(a) regulating the distance A between each of the microwave devices and the respective detectors of transmitted waves in the absence of the article so as to obtain in said detectors of transmitted waves a predetermined transmission signal level;

(b) readjusting said distance A in the absence of the article so as to obtain in said detectors of reflected waves a predetermined reflection signal level;

(c) fixing said distance A after said readjusting said distance A;

(d) placing the article in said support between said detectors of transmitted waves and microwave devices;

(e) regulating the distance B between said microwave devices and said support carrying the article so as to obtain in said detectors of reflected waves a reflection signal level substantially different from said predetermined reflection signal level; and, (f) fixing said distance B after said regulating the distance B.

13. A regulating method according to claim 12, whereby the distance A is regulated so as to obtain in the detectors of transmitted waves a maximum transmission signal level.

14. A regulating method according to one of the claim 12 or 13 whereby the distance A is readjusted so as to obtain a minimum reflection signal level in the detectors of reflected waves.

15. A regulating process according to claim 13, whereby the distance B is regulated so as to obtain in the detectors of reflected waves a maximum reflection signal level.

* * * * *

UNITED STATES PATENT AND TRADEMARK OFFICE
CERTIFICATE OF CORRECTION

PATENT NO. : 4,566,121
DATED : January 21, 1986
INVENTOR(S) : Johan Samyn

It is certified that error appears in the above-identified patent and that said Letters Patent is hereby corrected as shown below:

On the title page, Assignee should read -- N.V. Bekaert, S.A., Zwevegem, Belgium --.

Signed and Sealed this

Fifteenth Day of April 1986

[SEAL]

Attest:

DONALD J. QUIGG

*Attesting Officer*  Commissioner of Patents and Trademarks